US00PP16151P2

(12) United States Plant Patent
Geers

(10) Patent No.: US PP16,151 P2
(45) Date of Patent: Dec. 6, 2005

(54) ***ILEX* PLANT NAMED 'BLUE BARON'**

(50) Latin Name: *Ilex×meservae*
Varietal Denomination: Blue Baron

(75) Inventor: Gerald D. Geers, Ridgely, MD (US)

(73) Assignee: CP Delaware, Inc., Wilmington, DE (US)

( * ) Notice: Subject to any disclaimer, the term of this patent is extended or adjusted under 35 U.S.C. 154(b) by 59 days.

(21) Appl. No.: 10/879,098

(22) Filed: Jun. 30, 2004

(51) Int. Cl.[7] ..... A01H 5/00
(52) U.S. Cl. ..... Plt./247

(58) Field of Search ..... Plt./247

*Primary Examiner*—Anne Marie Grunberg
(74) *Attorney, Agent, or Firm*—Burns, Doane, Swecker & Mathis, LLP

(57) ABSTRACT

A new and distinct *Ilex×meservae* plant is provided that originated as a spontaneous mutation of unknown causation of the 'Blue Prince' variety (U.S. Plant Pat. No. 3,517). The foliage is dark green during the summer and unlike the 'Blue Prince' variety changes to an attractive Bordeaux coloration during the winter. The growth habit is dense, compact, vigorous and well-branched and commonly yields a smaller plant than the 'Blue Prince' variety. Good winter hardiness is displayed, and the plant is well suited for general landscape usage.

2 Drawing Sheets

Botanical/commercial classification: *Ilex×meservae/Ilex* Plant.

Varietal denomination: cv. 'Blue Baron'.

SUMMARY OF THE INVENTION

The new *Ilex* Plant was discovered during 1993 at Chance, Md., U.S.A., as a spontaneous branch mutation of unknown causation on a mature plant of the 'Blue Prince' variety (U.S. Plant Pat. No. 3,517).

The parent 'Blue Prince' variety was formed by the artificial crossing of an *Ilex aquifolium* seedling and an *Ilex rugosa* seedling, and is botanically classified as *Ilex× meservae* in honor of its originator, Kathleen K. Meserve.

Had the new plant of the present invention not been discovered and preserved it would have been lost to mankind. Following detailed observation it was found that this new plant exhibits the following combination of characteristics:

(a) displays a dense, compact, vigorous and well-branched growth habit that commonly yields a smaller plant than the 'Blue Prince' variety (U.S. Plant Pat. No. 3,517), (b) forms glossy dark green foliage during the summer that unlike the 'Blue Prince' variety changes to an attractive Bordeaux coloration during the winter, (c) exhibits good winter hardiness, and (d) is well suited for general landscape usage.

The new variety meets the needs of the horticultural industry and can be used to provide distinctive ornamentation in the landscape throughout the year. It can be used in a mass planting, as a hedge, or as a speciment plant.

The good winter hardiness has been confirmed by overwintering in containers above ground at West Grove, Pa., U.S.A.

The new variety can be readily distinguished from the parent 'Blue Prince' variety. More specifically, the 'Blue Prince' variety generally forms a larger less compact plant and displays foliage that assumes a blue-green coloration during the winter.

The new 'Blue Baron' variety of the present invention also can be readily distinguished from the 'Blue Angel' (U.S. Plant Pat. No. 3,662), 'Honey Maid' (U.S. Plant Pat. No. 12,060) and 'Willemer' (U.S. Plant Pat. No. 12,314) *Ilex* varieties. More specifically, the 'Blue Angel' unlike the 'Blue Baron' is a female with berry formation, is less winter hardy, and exhibits a considerably larger growth habit at maturity. The 'Honey Maid' variety is a female with berry formation, forms dissimilar variegated foliage, in recent years has been observed to be less winter hardy, and exhibits a slightly larger growth habit. Also, the 'Willemer' variety lacks the attractive Bordeaux winter foliage coloration of the 'Blue Baron' variety and tends during observations to date to form branches that are less supportive and to bend to a greater extent.

Asexual propagation of the new variety by the use of terminal semi-hardwood cuttings taken during July has been carried out at West Grove, Pa., U.S.A. Such propagation has confirmed that the combination of the characteristics of the new variety is stably established and is consistently transmitted to successive generations. The new cultivar reproduces true to type by such asexual propagation.

The new variety of the present invention has been named 'Blue Baron'.

BRIEF DESCRIPTION OF THE PHOTOGRAPHS

The accompanying photographs show as nearly true as it is possible to make the same in color illustrations of this character, typical specimens of the new variety. The photographs were obtained during the winter of 2005 near West Grove, Pa., U.S.A. The illustrated plants had been asexually reproduced by the rooting of cuttings.

DETAILED DESCRIPTION

Figure 1:
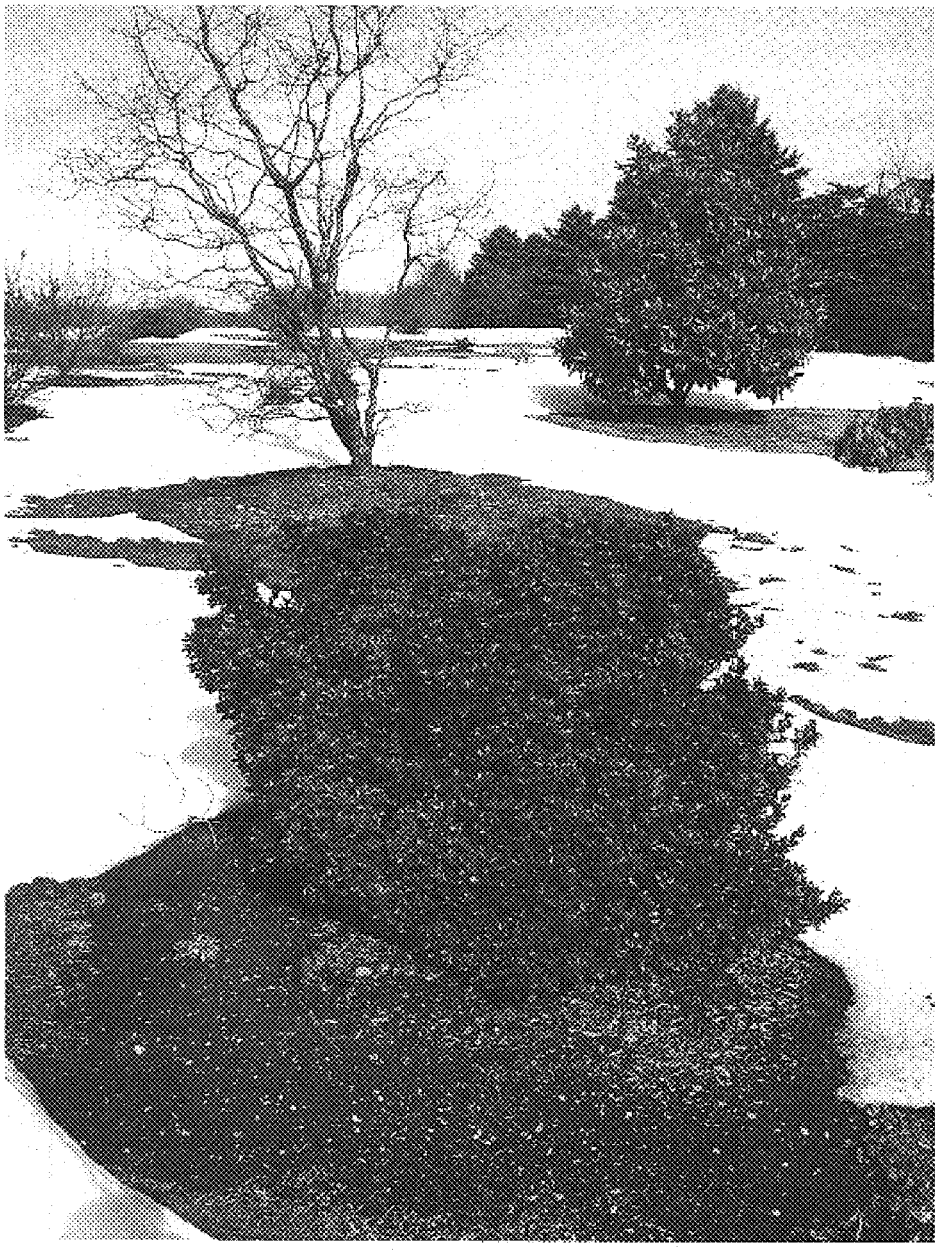
FIG. 1 illustrates an overall view of a mature approximately six year-old plant growing in the landscape wherein the dense, compact, vigorous and well-branched growth habit is illustrated.
Figure 2:
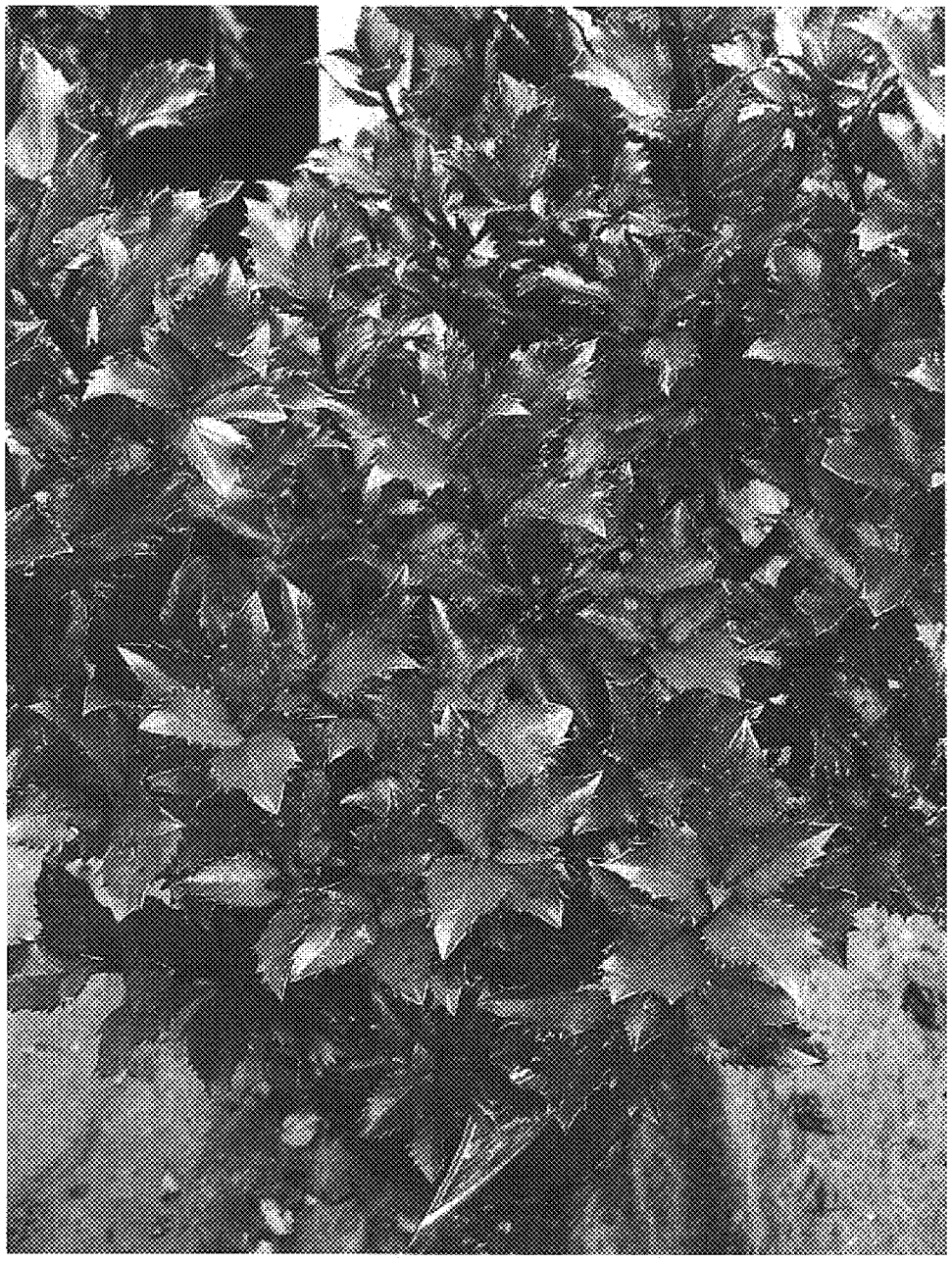
FIG. 2 illustrates a closer view of a plant wherein the foliage is shown in greater detail. The plant was approximately three years of age from a cutting, and was growing in a container in a protective hoop house.

The following is a detailed description of the new variety of the present invention while observing seven year-old plants being grown outdoors in containers at West Grove, Pa., U.S.A. Color terminology is in accordance with The R.H.S. Colour Chart of The Royal Horticultural Society, London, England, except where general color terms of ordinary dictionary significance are used.

Type: Hardy outdoor evergreen shrub for garden decoration and general landscape use.

Parentage: Spontaneous branch mutation of unknown causation of *Ilex aquifolium*×*Ilex rugosa*, cv. 'Blue Prince' (U.S. Plant Pat. No. 3,517).

Plant:

*Growth habit.*—Dense, compact, vigorous, and well-branched. Generally more compact than that of the 'Blue Prince' variety.

*Height.*—Approximately 2 to 2½ feet at an age of five years. At full maturity the plant will assume a height of approximately 4 feet. This can be compared to maximum height of approximately 12 feet for the 'Blue Prince' variety.

*Width.*—Approximately 2½ to 3 feet at an age of five years. At full maturity the plant will assume a height of approximately 6 feet. This can be compared to a maximum width of approximately 8 feet for the 'Blue Prince' variety.

Stems:

*Texture.*—Smooth.

*Color.*—Brown Group 200A on young stems, and Greyed-Purple Group 187A on mature stems.

*Lenticels.*—On a one year-old stem, oblong in configuration, generally flush with the surface, approximately 0.3 mm in length and approximately 0.2 mm in width, approximately 15 to 12 per square inch, and Orange-White Group 159A in coloration. On a three year-old stem, oblong in configuration, slightly eruptive or protruding above the surface, approximately 0.6 mm in length and approximately 0.5 mm in width, approximately 50 to 60 per square inch, and White Group 155D to Greyed-White Group 156D in coloration.

Foliage:

*Arrangement.*—Alternate.

*Shape.*—Elliptic.

*Apex.*—Acuminate.

*Base.*—Obtuse.

*Length.*—Approximately 5 to 6 cm on average.

*Width.*—Approximately 3 to 4 cm on average.

*Texture.*—On the upper surface smooth and glossy when juvenile and mature. On the under surface smooth and matte.

*Summer color.*—When juvenile, on the upper surface uniformly Green Group 137A, and on the under surface Yellow-Green Group 144A. When mature, on the upper surface uniformly Green Group 136A, and on the under surface Greyed-Green Group 191A and Greyed-Purple Group 185B.

*Venation.*—When juvenile, on the upper surface Green Group 141C to 141D, and on the under surface commonly bears some Red-Purple Group 59A approaching the base. When mature, on the upper surface Green Group 138D, and on the under surface Red-Purple Group 59A.

*Winter color.*—On both surfaces when juvenile and mature uniformly Bordeaux in coloration, ranging from Greyed-Purple Group 187A to 187C.

*Margins.*—Serrate.

*Spines.*—Leaves on lateral branches of current season's growth commonly possess approximately 10 to 18 spines on average, and leaves on main stems of current season's growth commonly possess approximately 17 to 23 spines on average.

*Petiole.*—Commonly approximately 0.5 cm in length, on the upper side commonly Yellow-Green Group 144B with some darker areas of Red-Purple Group 59B near the point of attachment to the leaf, and on the under side ranging from Red-Purple Group 59A with older leaves to Red-Purple Group 59C with younger leaves with some Yellow-Green Group 144B near the point of attachment to the stem.

Inflorescence:

*Type.*—Staminate.

*Bearing.*—Freely with several per stem in somewhat regular mounded clusters.

*Buds.*—Before the calyx breaks the floral buds are short, small, and globular without foliaceous appendages, and as the calyx breaks the initial petal coloration is Red Group 54C with the petal coloration changing to Red Group 56C as the flower continues to open.

*Petal count.*—Single petalage commonly with 4 or 5 petals.

*Petal texture.*—Relatively thin, soft, and satiny on both surfaces.

*Petal size.*—Approximately 2 mm.

*Flower shape.*—Cupped and globular.

*Flower size.*—Approximately 10 mm in diameter.

*Flower color.*—On the upper and under surfaces White Group 155B with tips of near Violet-Blue Group 91B.

*Fragrance.*—None.

Development:

*Hardiness.*—Very good, U.S.D.A. Hardiness Zone Nos. 5 to 9.

*Disease resistance.*—Generally comparable to that of the 'Blue Prince' variety with good resistance to Tar Spots (*Hasidim*) and Leaf Spot (*Cerocespora*) being exhibited.

*Pest resistance.*—Good with respect to Leaf Miner.

Plants of the new 'Blue Baron' variety have not been observed under all possible environmental conditions to date. Accordingly, it is possible that the phenotypic expression may vary somewhat with changes in light intensity and duration, cultural practices, and other environmental conditions.

I claim:

1. A new and distinct *Ilex*×*meservae* plant having the following combination of characteristics:

(a) displays a dense, compact, vigorous and well-branched growth habit that commonly yields a smaller plant than the 'Blue Prince' variety (U.S. Plant Pat. No. 3,517), (b) forms glossy dark green foliage during the summer that unlike the 'Blue Prince' variety changes to an attractive Bordeaux coloration during the winter, (c) exhibits good winter hardiness, and (d) is well suited for general landscape usage;

substantially as illustrated and described.

* * * * *